United States Patent [19]

Chung

[11] Patent Number: 5,138,734
[45] Date of Patent: Aug. 18, 1992

[54] MOTOR-OPERATED TOOTHBRUSH BRISTLE FASTENING STRUCTURE

[76] Inventor: Chin-Fu Chung, No. 18, Hsin Hsin Road, Tainan City, Taiwan

[21] Appl. No.: 727,025
[22] Filed: Jul. 8, 1991
[51] Int. Cl.⁵ ............................ A61C 17/16; A46B 13/02
[52] U.S. Cl. .......................................... 15/28; 15/167.1; 15/180
[58] Field of Search ................. 15/22.1, 28, 29, 167.1, 15/180; 433/125

[56] References Cited
U.S. PATENT DOCUMENTS
5,068,939 12/1991 Holland .................................. 15/28
5,070,567 12/1991 Holland .................................. 15/28

*Primary Examiner*—Edward L. Roberts
*Attorney, Agent, or Firm*—Varndell Legal Group

[57] ABSTRACT

A motor-operated toothbrush bristle fastening structure, comprising a brush head having two rows of stub rods fixedly disposed at two opposite sides, a plurality of gears respectively mounted on said stub rods with the ones on the same row of stub rods respectively engaged with one another and driven by a screw rod to carry a plurality of rotary wheels to rotate, which rotary wheels have each a bundle of bristles fastened therein for cleaning the teeth, and a plurality of spring coils respectively fastened in said gears to resiliently support said rotary wheels permitting the bundles of bristles to be moved up and down when they are carried by said rotary wheel and driven by said gears to rotate on said stub rods.

1 Claim, 2 Drawing Sheets

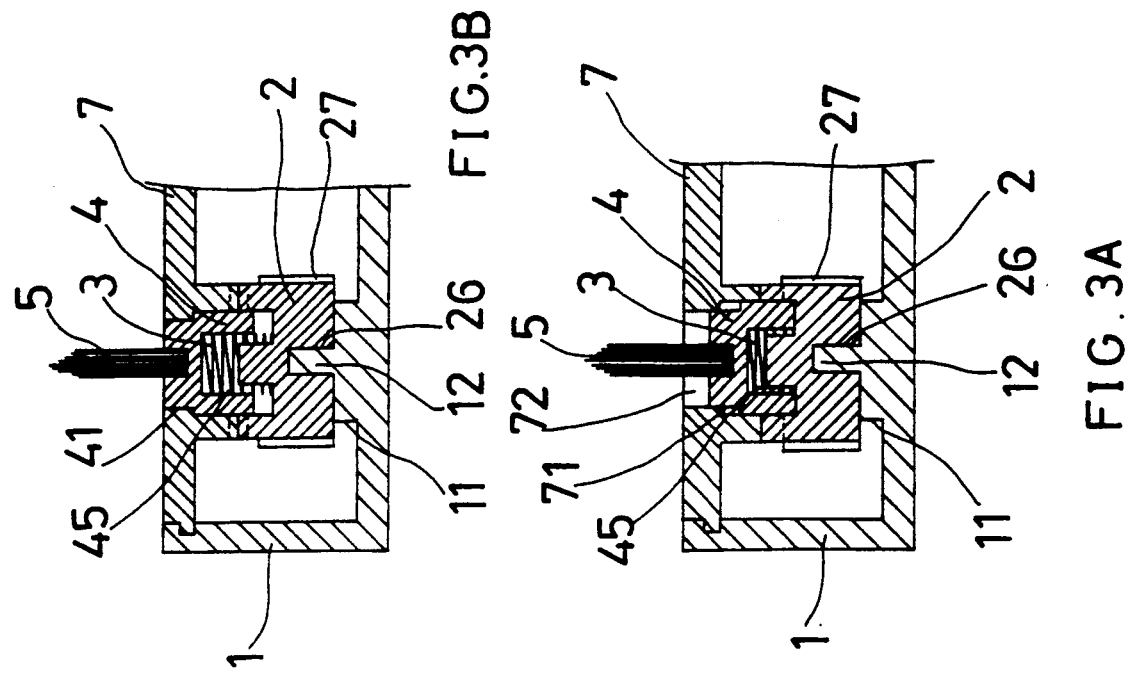
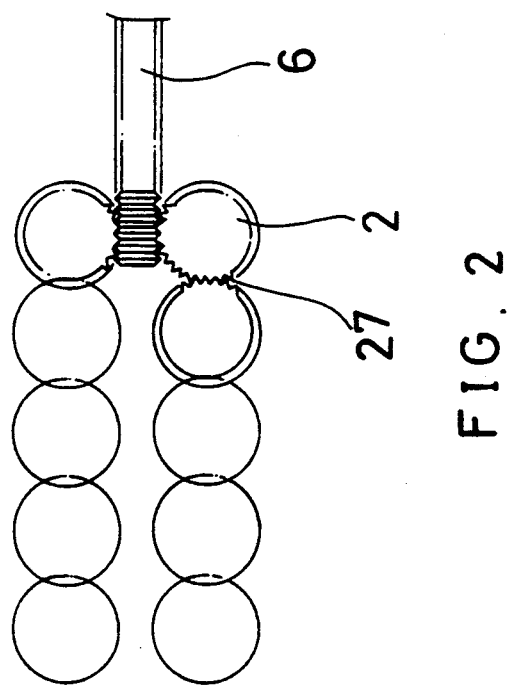

MOTOR-OPERATED TOOTHBRUSH BRISTLE FASTENING STRUCTURE

BACKGROUND OF THE INVENTION

The present invention relates to motor-operated toothbrushes and relates more particularly to a bristle fastening structure for a motor-operated toothbrush which has a plurality of bundles of bristles fastened in a plurality of rotary wheels which are resiliently supported by a plurality of spring coils and driven by two rows of gears to carry said bundles of bristles to rotate and float thereon while cleaning the teeth.

Conventionally, a toothbrush generally comprises a handle having a brush head longitudinally disposed at one end with a plurality of bundles of bristles fixedly fastened therein. In recent years, various types of motor-operated toothbrushes have been disclosed. According to the known structures of motor-operated toothbrushes, the bundles of bristles are respectively fastened in rotary members and driven by a transmission device to rotate on their own axes respectively. Neither of the aforesaid toothbrush structures is satisfactory in use. Disadvantages of the aforesaid toothbrush structures are numerous and outlined hereinafter.

1. The gums may be injured easily during teeth cleaning process. For removing dirt from the gaps in the teeth, certain force must be applied to the bristles. Because no resilient means to support the bundles of bristles, the gums may be injured by the bristles easily when excessive force is applied thereto.

2. The bristles may be deformed and damaged easily. Because no resilient means to support the bundles of bristles, constantly rubbing the bristles against the teeth causes the bristles to deform quickly.

3. The enamel coating of teeth may be damaged easily when cleaning the teeth with excessive force.

4. Satisfactory cleaning effect is difficult to achieve. Because the bristles are fixedly or just rotatably fastened in the brush head, they can not be conveniently repeatedly moved in and out of the gaps in the teeth to thoroughly remove the dirt therefrom.

SUMMARY OF THE INVENTION

The present invention has been accomplished to eliminate the aforesaid disadvantages. According to the present invention, there is provided a motor-operated toothbrush comprising a brush head having two rows of stub rods fixedly disposed at two opposite sides, a plurality of gears respectively mounted on said stub rods with the ones on the same row of stub rods respectively engaged with one another and driven by a screw rod to carry a plurality of rotary wheels to rotate, which rotary wheels have each a bundle of bristles fastened therein for cleaning the teeth, and a plurality of spring coils respectively fastened in said gears to resiliently support said rotary wheels permitting the bundles of bristles to be moved up and down when they are carried by said rotary wheel and driven by said gears to rotate on said stub rods. Because of the effect of the spring coils, the bundles of bristles can be conveniently moved in and out of the gaps in the teeth when they are driven to resiliently rub dirt away from the teeth.

A motor-operated toothbrush constructed in accordance with the present invention can achieve the following advantages:

1. The gums prohibited from damage during teeth cleaning operation. Any excessive force applied to the bristles will be reduced by the spring force from the spring coils during teeth cleaning operation, and therefore, the gums will not be damaged.

2. The bristles will not be caused to deform quickly. Because any excessive force to the bristles during teeth cleaning operation will be reduced by the spring force from the spring coils, cleaning the teeth does not cause the bristles to deform quickly.

3. The enamel coating of teeth will not be damaged easily. Because no excessive rubbing force will be applied to the enamel coating of teeth while cleaning the teeth, the enamel coating of teeth will not be damaged easily.

4. Satisfactory cleaning result can be achieved. Because the bristles can be conveniently moved up and down to move in and out of the gaps in the teeth while they are carried to rotate for rubbing dirt away from the teeth, dirt on the teeth as well as in the gaps between teeth can be completely removed.

BRIEF DESCRIPTION OF THE DRAWINGS

FIG. 2 illustrates the transmission of the screw rod in driving two rows of gears to rotate;

FIG. 3A is a sectional view showing that a bundle of bristles is fastened in a rotary wheel which is supported by a spring coil and carried to rotate by a gear;

FIG. 3B illustrates that each bundle of bristles is resiliently supported by a spring coil and permitted to move up and down.

DETAILED DESCRIPTION OF THE PREFERRED EMBODIMENT

Figures 1A, 1B:
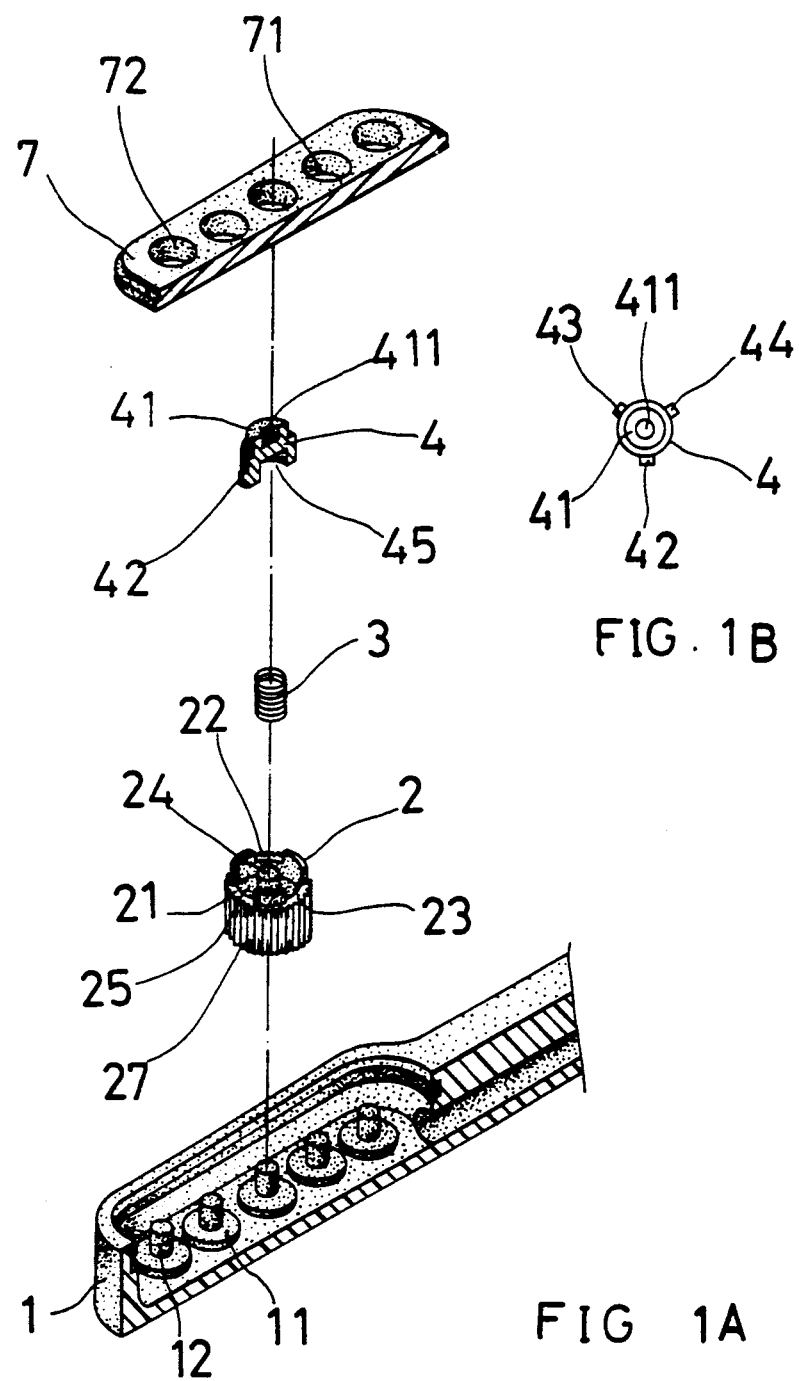
FIG. 1A is an exploded, partly perspective view of the preferred embodiment of the present invention.
FIG. 1B is a top view of the rotary wheel.

Referring to FIGS. 1A and 1B, the present invention is generally comprised of a brush head 1, a plurality of gears 2, a plurality of spring coils 3, a plurality of rotary wheels 4, a plurality of bundles of bristles 5, a screw rod 6 and an upper cap 7. The brush head 1 is a hollow structure longitudinally extending from a handle at one end, having two rows of raised portions 11 raising from the inner bottom thereof at two opposite sides, which two rows of raised portions 11 have each a stub rod 12 vertically disposed at the center for holding a gear 2 each. Each gear 2 has a plurality of teeth 27 around the periphery thereof, three notches 21, 22 and 23 equidistantly made on the top edge thereof, a recess 25 at the top surrounded by said notches 21, 22 and 23, a shaft 24 vertically raising from said recess 25 at the center for holding a spring coil 3, and a blind hole 26 at the bottom. The rotary wheels 4 are respectively mounted on the gears 2 for holding a bundle of bristles 5 each. Each rotary wheel 4 comprises a top projection 41 having a round hole 411 at the center for fastening a bundle of bristles 5, a recessed hole 45 at the bottom for holding a spring coil 3, and three side projecting blocks equidistantly projecting outwards from the bottom edge thereof and disposed at locations corresponding to the three notches 21, 22 and 23 on each gear 2. The upper cap 7 is made in size suitable for covering the top opening of the brush head 1, having two rows of round holes 72 corresponding to the two rows of raised portions 11, which round holes 72 have each a recessed hole 71 at the bottom into which the top projection 41 of each rotary wheel 4 is engaged.

Referring to FIGS. 2, 3A and 3B, the gears 2 which are mounted on the stub rods 12 on either row of raised portions 11 are respectively engaged with one another. When the screw rod 6 which is simultaneously engaged with the first one of each of the two rows of gears 2 is driven by a motor to rotate, the gears 2 are simultaneously driven to rotate, causing the rotary wheels 4 to carry the bundles of bristles 5 to rotate. Because of the effect of the spring coils 3, the bundles of bristles 5 which are respectively fastened in the rotary wheels 4 are permitted to resiliently move up and down relative to the gears 2 when they are carried to rotate and moved to clean the teeth.

I claim:

1. A motor-operated toothbrush bristle fastening structure, comprising:

a brush head defining therein an elongated, recessed hole having two rows of raised portions longitudinally disposed at two opposite sides, said raised portions having each a stub rod vertically disposed at the center;

a plurality of gears respectively mounted on the stub rod of each of said raised portions, having each a plurality of notches equidistantly made on the top edge thereof, a recess at the top surrounded by said notches, a shaft vertically raising from said recess at the center, and a blind hole at the bottom for inserting said stub rod, the gears mounted on either one of said two rows of raised portions being engaged with one another;

a plurality of rotary wheels respectively mounted on said gears and carried by said gears to rotate on said raised portions, comprising a top projection at the top, said top projection having a round hole at the center with a bundle of bristles fastened therein, a recessed hole at the bottom, and a plurality of side projecting blocks equidistantly projecting outwards from the bottom edge thereof and respectively engaged in the notches on each of said gears;

an upper cap covered on the elongated, recessed hole of said brush head, having two rows of through holes corresponding to said two rows of raised portions through which the bundles of bristles from said rotary wheels extend out of said brush head, said through holes having each a recessed hole at the bottom into which the top projection on each of said rotary wheel is engaged; and characterized in that a spring coil each is mounted on the shaft on each of said gears and received in the recessed hole on the bottom of each of said rotary wheel to resiliently support each of said rotary wheels on each of said gears permitting the bundles of bristles to be moved up and down on said rotary wheel during rotary motion.

* * * * *